United States Patent [19]

Sih

[11] 4,277,613
[45] Jul. 7, 1981

[54] 19-HYDROXY-19-METHYL-6-OXO-PGF₁ INTERMEDIATES

[75] Inventor: John C. Sih, Portage, Mich.

[73] Assignee: The Upjohn Company, Kalamazoo, Mich.

[21] Appl. No.: 126,504

[22] Filed: Mar. 3, 1980

Related U.S. Application Data

[62] Division of Ser. No. 54,720, Jul. 5, 1979, Pat. No. 4,225,507.

[51] Int. Cl.³ .............................................. C07C 177/00
[52] U.S. Cl. .................................... 560/121; 562/503
[58] Field of Search ........................ 560/121; 562/503

[56] References Cited

U.S. PATENT DOCUMENTS 4,054,595  10/1977  Marx .................................... 560/121

*Primary Examiner*—Robert Gerstl
*Attorney, Agent, or Firm*—Robert A. Armitage

[57] ABSTRACT

The present invention provides novel 19-hydroxy-19-methyl-6-oxo-PGF₁ intermediates for preparing prostacyclin analogs which are useful for pharmacological purposes, e.g., anti-asthmatic indications.

1 Claim, No Drawings

19-HYDROXY-19-METHYL-6-OXO-PGF₁ INTERMEDIATES

CROSS REFERENCE TO RELATED APPLICATION

The present invention is a divisional application of U.S. Ser. No. 054,720, filed July 5, 1979, now U.S. Pat. No. 4,225,507.

DESCRIPTION

1. Background of the Invention

The present invention provides novel prostacyclin analogs. Particularly, the present invention relates to prostacyclin analogs substituted at the C-19 position by hydroxy.

Particularly, the present invention relates to 19-hydroxy-19-methyl-6-oxo-PGF$_1$ intermediates for preparing these protacyclin analogs. The novel prostacyclin analogs are useful for pharmacological purposes, e.g., as anti-asthmatic agents. The preparation and use of these compounds is incorporated here by reference from U.S. Pat. No. 4,225,507.

2. Prior Art

For background on prostacyclin, see for example R. A. Johnson, et al., Prostaglandins 12, 915-928 (1976) and R. A. Johnson, et al., J. Am. Chem. Soc. 100, 7690-7704 (1978), and, as to pharmacological activity, the references cited therein. For analogs of prostacyclin, see, for example, J. Fried, et al., Proc. Natl. Acad. Sci. U.S.A,. 74, 2199-2203, K. C. Nicolaou, et al., J.C.S. Chem. Comm. 1977, 331-332, N. A. Nelson, J. Am. Chem. Soc. 99, 7362-7363 (1977), and K. Kojima, et al., Tetra. Letters, 1978, (1977), and K. Kojima, et al., Tetra. Letters, 1978, 3743-3746. Regarding the nomenclature for analogs of PGI$_2$, see R. A. Johnson, et al., Prostaglandins 15, 737-740 (1978).

SUMMARY OF THE INVENTION

The present invention particularly provides a prostacyclin-type compound of the formula

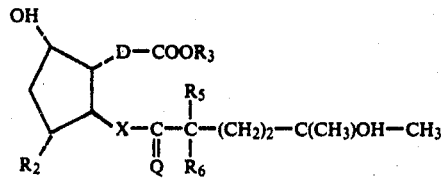

wherein D is —(CH$_2$)$_2$—CO—CH$_2$—L$_2$— or —CH$_2$—CO—CH$_2$—L$_3$—;
wherein L$_2$ is
 (1) —(CH$_2$)$_j$— wherein j is one to 4, inclusive,
 (2) —(CH$_2$)$_q$—CF$_2$— wherein q is one, 2, or 3, or
 (3) —CH=CH—,
wherein L$_3$ is
 (1) —(CH$_2$)$_n$— wherein n is one to 5, inclusive,
 (2) —(CH$_2$)$_p$—CF$_2$— wherein p is 2, 3, or 4, and
 (3) —CH$_2$CH=CH—,
wherein Q is oxo, α-H:β-H, α-OH:β-R$_4$, or α-R$_4$:β-OH;
wherein R$_4$ is hydrogen or alkyl of one to 4 carbon atoms, inclusive;
wherein R$_3$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive;
 (g) —(Ph)—CO—CH$_3$,
 (h) —(p-Ph)—NH—CO—(p-Ph)—NH—CO—CH$_3$,
 (i) —(p-Ph)—NH—CO—(p-Ph),
 (j) —(p-Ph)—NH—CO—CH$_3$,
 (k) —(p-Ph)—NH—CO—NH$_2$,
 (l) —(p-Ph)—CH—N—NH—CO—NH$_2$,
 (m) β-naphthyl,
 (n) —CH$_2$—CO—R$_{16}$,
wherein —(Ph)— is inter-phenylene and —(p-Ph) is inter-para-phenylene or para-phenyl;
wherein R$_{16}$ is phenyl, p-bromophenyl, p-biphenylyl, p-nitrophenyl, p-benzamidophenyl, or 2-naphthyl, or
(o) a pharmacologically acceptable cation;
wherein R$_2$ is hydrogen, hydroxyl, or hydroxymethyl,
 wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and
wherein X is
 (1) trans-CH=-,
 (2) cis-CH=CH-,
 (3) —C≡C—, or
 (4) —CH$_2$CH$_2$—,
and wherein ∼indicates attachment in alpha or beta configuration.

I claim:

1. A prostacyclin-type compound of the formula

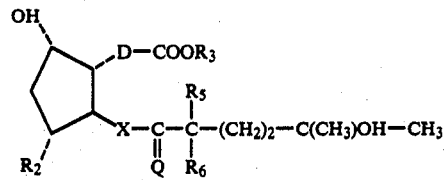

wherein D is —(CH$_2$)$_2$—CO—CH$_2$—L$_2$— or —CH$_2$—CO—CH$_2$—L$_3$—;
wherein L$_2$ is
 (1) —(CH$_2$)$_j$— wherein j is one to 4, inclusive,
 (2) —(CH$_2$)$_q$—CF$_2$— wherein q is one, 2, or 3, or
 (3) —CH=CH—,
wherein L$_3$ is
 (1) —(CH$_2$)$_n$— wherein n is one to 5, inclusive,
 (2) —(CH$_2$)$_p$—CF$_2$— wherein p is 2, 3, or 4, or
 (3) —CH$_2$CH=CH—,
wherein Q is oxo, α-H:β-H, α-OH:β-R$_4$, or α-R$_4$:β-OH,
wherein R$_4$ is hydrogen or alkyl of one to 4 carbon atoms, inclusive;
wherein R$_3$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive,
 (g) —(Ph)—CO—CH$_3$,
 (h) —(p-Ph)—NH—CO—(p-Ph)—NH—CO—CH$_3$,
 (i) —(p-Ph)—NH—CO—(p-Ph),
 (j) —(p-Ph)—NH—CO—CH$_3$,
 (k) —(p-Ph)—NH—CO—NH$_2$, (l) -(p-Ph)-CH=N-NH-CO-NH$_2$, (m) β-naphthyl, (n) —CH$_2$—CO—R$_{16}$, wherein —(Ph)— is inter-phenylene and —(p-Ph) is inter-para-phenylene or para-phenyl;

wherein R$_{16}$ is phenyl, p-bromophenyl, p-biphenylyl, p-nitrophenyl, p-benzamidophenyl, or 2-naphthyl, or (o) a pharmacologically acceptable cation;

wherein R$_2$ is hydrogen, hydroxyl, or hydroxymethyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and wherein X is (1) trans-CH=CH-, (2) cis-CH=CH-, (3) —C≡C—, or (4) —CH$_2$CH$_2$—, and wherein ∼ indicates attachment in alpha or beta configuration.

* * * * *

UNITED STATES PATENT OFFICE
CERTIFICATE OF CORRECTION

Patent No.  4,277,613          Dated    7 July 1981

Inventor(s)   John C. Sih

It is certified that error appears in the above-identified patent and that said Letters Patent are hereby corrected as shown below:

Column 2, line 10, "-(p-Ph)-CH-N-NH-CO-$NH_2$" should read -- -(p-Ph)-CH=N-NH-CO-$NH_2$ --; line 24, "trans-CH=-," should read -- trans-CH=CH-, --; line 26, "-C=C-" should read -- -C≡C- --.

Signed and Sealed this

Twenty-seventh Day of October 1981

[SEAL]

Attest:

GERALD J. MOSSINGHOFF

Attesting Officer            Commissioner of Patents and Trademarks